US010292375B1

(12) United States Patent
Massaro et al.

(10) Patent No.: US 10,292,375 B1
(45) Date of Patent: *May 21, 2019

(54) PUPAE EMERGENCE APPARATUS

(71) Applicant: Verily Life Sciences LLC, South San Francisco, CA (US)

(72) Inventors: Peter Massaro, San Carlos, CA (US); Robert Sobecki, Brisbane, CA (US); Tiantian Zha, South San Francisco, CA (US); Brian Wasson, Columbus, OH (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/055,253

(22) Filed: Aug. 6, 2018

Related U.S. Application Data

(63) Continuation of application No. 15/285,623, filed on Oct. 5, 2016, now Pat. No. 10,051,845.

(51) Int. Cl.
*A01K 67/00* (2006.01)
*A01K 29/00* (2006.01)
*A01K 67/033* (2006.01)
*B01D 35/02* (2006.01)

(52) U.S. Cl.
CPC .......... *A01K 67/033* (2013.01); *A01K 29/005* (2013.01); *B01D 35/02* (2013.01)

(58) Field of Classification Search
CPC .................................................. A01K 67/033
USPC ......................................... 119/6.5, 236, 421
See application file for complete search history.

(56) References Cited

U.S. PATENT DOCUMENTS

| 3,223,237 A | 12/1965 | Harrod, Jr. et al. |
| 3,468,289 A | 9/1969 | Broida |
| 3,750,625 A * | 8/1973 | Edwards ............... A01K 67/033 119/322 |
| 4,144,668 A | 3/1979 | Darncharnjitt et al. |
| 4,212,267 A * | 7/1980 | Patterson ............. A01K 67/033 119/421 |
| 4,368,690 A * | 1/1983 | Tenzer ................. A01K 67/033 119/496 |

(Continued)

FOREIGN PATENT DOCUMENTS

| CN | 102499182 | 6/2012 |
| CN | 202285912 | 7/2012 |

(Continued)

OTHER PUBLICATIONS

U.S. Appl. No. 15/285,642, "Non-Final Office Action", dated Aug. 9, 2018, 5 pages.

(Continued)

*Primary Examiner* — Yvonne R Abbott-Lewis
(74) *Attorney, Agent, or Firm* — Kilpatrick Townsend & Stockton LLP

(57) ABSTRACT

An apparatus may include a vessel having an interior space to receive water and insect pupae. The apparatus may include a release container connected to the vessel and a sensor positioned proximate to the release container to detect an adult insect passing by the sensor and into the release container. A shutter may be positioned proximate to an entrance to the release container. The shutter may have an open position and a closed position to control access between the vessel and the release container.

20 Claims, 5 Drawing Sheets

(56) References Cited

U.S. PATENT DOCUMENTS

| | | | |
|---|---|---|---|
| 4,417,545 A | 11/1983 | Finney | |
| 4,523,404 A | 6/1985 | DeYoreo et al. | |
| 4,646,683 A | 3/1987 | Maedgen, Jr. | |
| 4,765,275 A | 8/1988 | Yukawa et al. | |
| 4,785,764 A | 11/1988 | Muller | |
| 4,863,693 A | 9/1989 | Howell | |
| 5,074,247 A | 12/1991 | Gupta et al. | |
| 5,178,094 A | 1/1993 | Carr et al. | |
| 5,351,643 A * | 10/1994 | Hughes | A01K 67/033 119/6.5 |
| RE35,348 E | 10/1996 | Georgi | |
| 5,594,654 A | 1/1997 | Shuman et al. | |
| 5,784,991 A | 7/1998 | Ukishiro et al. | |
| 5,819,685 A | 10/1998 | Kappelt et al. | |
| 6,244,213 B1 | 6/2001 | Tedders et al. | |
| 6,293,223 B1 | 9/2001 | Eberts et al. | |
| 6,557,487 B1 | 5/2003 | Fleischmann | |
| 6,653,971 B1 | 11/2003 | Guice et al. | |
| 6,688,255 B2 * | 2/2004 | Donaldson | A01K 67/033 119/6.5 |
| 6,766,251 B2 | 7/2004 | Mafra-Neto et al. | |
| 7,861,672 B2 * | 1/2011 | Power | A01K 61/54 119/236 |
| 8,322,304 B2 | 12/2012 | Chung | |
| 9,295,245 B1 | 3/2016 | Guice et al. | |
| 9,510,572 B2 | 12/2016 | Aldana et al. | |
| 9,594,162 B1 | 3/2017 | Sonera et al. | |
| 9,642,344 B2 * | 5/2017 | Unger | A01K 67/033 |
| 2002/0035444 A1 | 3/2002 | Wilkerson et al. | |
| 2002/0185605 A1 | 12/2002 | Shuman et al. | |
| 2006/0196427 A1 * | 9/2006 | Lepori | A01K 1/0245 119/6.6 |
| 2012/0017834 A1 | 1/2012 | Holland et al. | |
| 2013/0083974 A1 | 4/2013 | Tsai et al. | |
| 2013/0204581 A1 | 8/2013 | Park et al. | |
| 2013/0319334 A1 | 12/2013 | Newton et al. | |
| 2014/0123902 A1 | 5/2014 | Kitazumi et al. | |
| 2018/0092339 A1 | 4/2018 | Massaro et al. | |
| 2018/0206464 A1 | 7/2018 | Massaro et al. | |
| 2018/0206465 A1 | 7/2018 | Massaro et al. | |
| 2018/0206473 A1 | 7/2018 | Massaro et al. | |

FOREIGN PATENT DOCUMENTS

| | | |
|---|---|---|
| CN | 105409893 | 3/2016 |
| WO | 2010038055 | 4/2010 |
| WO | 2015126855 | 8/2015 |
| WO | 2016024164 | 2/2016 |
| WO | 2018067376 | 4/2018 |

OTHER PUBLICATIONS

U.S. Appl. No. 15/285,623 , "Notice of Allowance", dated Apr. 16, 2018, 9 pages.

Carvalho et al., "Mass production of genetically modified Aedes aegypti for field releases in Brazil", Journal of visualized experiments: JoVE 83 (2014).

PCT/US2017/054094 , "International Search Report and Written Opinion", dated Nov. 29, 2017, 12 pages.

U.S. Appl. No. 15/285,624 , "Non-Final Office Action", dated Jan. 14, 2019, 10 pages.

U.S. Appl. No. 15/285,642 , "Notice of Allowance", dated Jan. 23, 2019, 7 pages.

U.S. Appl. No. 15/285,866 , "Notice of Allowance", dated Dec. 31, 2018, 7 pages.

U.S. Appl. No. 15/285,866 , "Supplemental Notice of Allowance", dated Jan. 10, 2019, 2 pages.

Liu et al., "A Review of Recent Sensing Technologies to Detect Invertebrates on Crops", Precision Agriculture, vol. 18, No. 4, Aug. 31, 2016, 38 pages.

Roberto et al., "Doppler Radar Signatures of Migrating Birds", Available online at https://ams.confex.com/ams/pdfpapers/21432.pdf https://ams.confex.com/ams/30radar/techprogram/paper_21432.htm, Jul. 20, 2001, 3 pages.

* cited by examiner

PUPAE EMERGENCE APPARATUS

CROSS-REFERENCE TO RELATED APPLICATION

This application is a continuation of U.S. patent application Ser. No. 15/285,623, filed Oct. 5, 2016, titled "Pupae Emergence Apparatus," which is incorporated herein by reference in its entirety.

TECHNICAL FIELD

The present disclosure generally relates to pupae emergence apparatus, and, more particularly, although not necessarily exclusively, to pupae emergence apparatus that may be coupled to multiple release containers.

BACKGROUND

Mosquito pupae may be placed in a vessel in which the pupae develop into adult mosquitos. The adult mosquitos may be transferred manually from the vessel to a release container. Mosquito sterile insect technique programs may need to release a known number of adult mosquitos from the release container.

SUMMARY

In some aspects of the present disclosure, an emergence apparatus may include a vessel that has an interior space to receive water and insect pupae. A first passageway may connect the vessel to the first release container. A first sensor may be positioned proximate to the first release container to detect an adult insect passing by the first sensor and into the first release container. A second passageway may be positioned proximate to the second release container to detect an adult insect passing by the second sensor and into the second release container. A first shutter may be positioned in the first passageway. The first shutter may have an open position and a closed position to control access between the vessel and the first release container. A second shutter may be positioned in the second passageway, the second shutter may have an open position and a closed position to control access between the vessel and the second release container. A computing device may be configured to receive a first input signal from the first sensor and a second input signal from the second sensor. The first shutter may be configured to receive a first output signal from the computing device to position the first shutter in one of the open position or the closed position. The second shutter may be configured to receive a second output signal from the computing device to position the second shutter in one of the open position or the close position.

In some aspects, an emergence apparatus may include a vessel that has an interior space to receive water and insect pupae. A first passageway may connect the vessel to the first release container. A first sensor may be positioned proximate to the first release container to detect an adult insect passing by the first sensor and into the first release container. A second passageway may be positioned proximate to the second release container to detect an adult insect passing by the second sensor and into the second release container. A first shutter may be positioned in the first passageway. The first shutter may have an open position and a closed position to control access between the vessel and the first release container. A second shutter may be positioned in the second passageway, the second shutter may have an open position and a closed position to control access between the vessel and the second release container. A first computing device may be configured to receive a first input signal from the first sensor. A second computing device may be configured to receive a second input signal from the second sensor. The first shutter may be configured to receive a first output signal from the first computing device to position the first shutter in one of the open position or the closed position. The second shutter may be configured to receive a second output signal from the second computing device to position the second shutter in one of the open position or the close position.

In some aspects, a method may include providing an emergence apparatus that may include a vessel that has an interior space to receive water and insect pupae. The apparatus may include a first passageway that connects the vessel to a first release container. A first sensor may be positioned proximate to the first release container to detect an adult insect passing by the first sensor and into the first release container. A second passageway may connect the vessel to a second release container. A second sensor may be positioned proximate to the second release container to detect an adult insect passing by the second sensor and into the second release container. A first shutter may be positioned in the first passageway. The first shutter may have an open position and a closed position to control access between the vessel and the first release container. A second shutter may be positioned in the second passageway, the second shutter may have an open position and a closed position to control access between the vessel and the second release container. The method may include detecting, by at least one of the first sensor or the second sensor, an adult insect has passed by either the first sensor or the second sensor. The sensor that has detected an insect may transmit a signal to a computing device. The signal may indicate an adult insect has passed by the sensor. The computing device may determine a total number of adult insects that have passed by the sensor that transmitted the signal.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
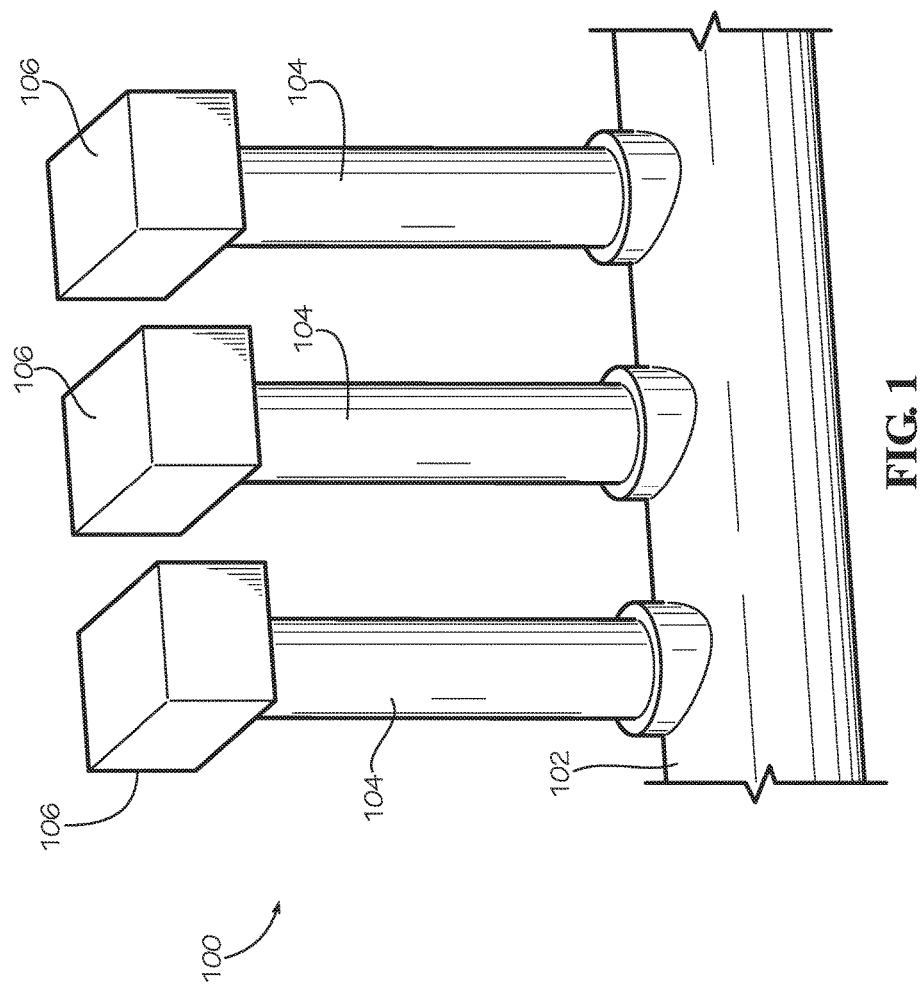
FIG. 1 is a perspective view of a pupae emergence apparatus coupled to release containers, according to aspects of the present disclosure.

Certain aspects and examples of the present disclosure relate to an emergence apparatus for raising mosquito pupae into adult mosquitos. The emergence apparatus is coupleable to multiple release containers. The emergence apparatus can control the number of adult mosquitos that may enter each of the release containers. The emergence apparatus includes a vessel, such as a pipe, that receives water and mosquito pupae. Multiple passageways may connect the vessel to multiple release containers. As the mosquito pupae develop into adult mosquitos in the pipe they can fly through any one of the passageways and into the release container coupled to the vessel via the passageway.

The emergence apparatus may also include a sensor at the end of each of the passageway near the release container. Each sensor can determine when an adult mosquito has passed by the sensor and entered the respective release container. The emergence apparatus can also include a shutter positioned within or near each passageway. The shutter can open and close to control access to the release container coupled to the vessel via the passageway.

Each sensor can determine the total number of adult mosquitos that have passed by the respective sensor and entered the attached release container. The sensor within a particular passageway can send a signal to the shutter positioned in or near the same passageway to open or close based on the total number of adult mosquitos that have passed by the sensor and entered the release container. For example, the sensor can send a signal to the shutter to move to the closed position if the sensor determines that a certain number of adult mosquitos have entered the respective release container. With the shutter of a particular passageway in the closed position, the adult mosquitos in the release container attached to the vessel via the passageway may not be able to leave the release container, and other adult mosquitos in the passageway may not be able to enter the attached release container.

In some aspects, the sensor may be communicatively coupled to a computing device located away from the sensor. The computing device may be a controller, a counter, or a computing device that includes a processor and a non-transitory computer readable medium comprising processor-executable instructions.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure. The various figures described below depict examples of implementations for the present disclosure, but should not be used to limit the present disclosure.

FIG. 1 is a perspective view of an emergence apparatus 100 for storing pupae as they develop into adult mosquitos according to an aspect of the present disclosure. In some aspects, the pupae of other insects may be raised from pupae to adulthood in the emergence apparatus 100. The emergence apparatus 100 may include a vessel, such as a pipe 102 in which pupae and water may be placed. The emergence apparatus 100 may also include one or more passageways that connect the pipe 102 to one or more release containers 106. The passageways may be short or long in length. For example the passageway may be a tube 104 that extends from the pipe 102. As shown in FIG. 1, release containers 106 may be coupled to the tubes 104 of the emergence apparatus 100. The tubes 104 may form a passageway between an interior region of the pipe 102 and an interior region of the release containers 106. In some aspects, the release container 106 may be coupled directly to the pipe 102. In such aspects, the passageway may be the opening between the release container 106 and the pipe 102.

The pupae may emerge into adult mosquitos within the pipe 102. The adult mosquitos may fly from the pipe 102 through the tubes 104 and into the release containers 106. A shutter or valve (not shown) may control access from the tubes 104 to the release containers 106. The shutter may restrict access from the tube 104 to the release container 106 in response to a sensor determining that a desired number of adult mosquitos are in the release container 106.

The release containers 106 may be coupled to the tubes 104 of the emergence apparatus 100, for example but not limited to, by threaded engagement, by an adhesive, by hook and loop fasteners, or by snap-fit engagement. The release containers 106 may be removable from the tubes 104. Though FIG. 1 depicts the emergence apparatus 100 including three tubes 104 and three release containers 106, more or fewer tubes 104 and release containers 106 may be used. The release containers 106 may include attractants or features that attract the adult mosquitos (or other insects) to fly into the release containers 106, for example but not limited to sounds that attract adult mosquitos or other insects. In some aspects, a sound that corresponds to the wing beat frequency of a female mosquito may be played inside or proximate to the release container 106, this sound may attract male mosquitos to the release container 106. In some aspects, a scent or scents may be positioned within the release container 106 to attract adult mosquitos or other insects. In some aspects, the scent or scents may attract a particular sex of an insect. The pipe 102 of the emergence apparatus 100 may be manufactured from materials that are suitable for containing water and raising pupae into adult mosquitos (or other adult insects), for example but not limited to polyvinyl chloride ("PVC"), aluminum, or stainless steel. The tubes 104 may also be manufactured from PVC, aluminum, stainless steel, or other suitable materials.

Figure 2:
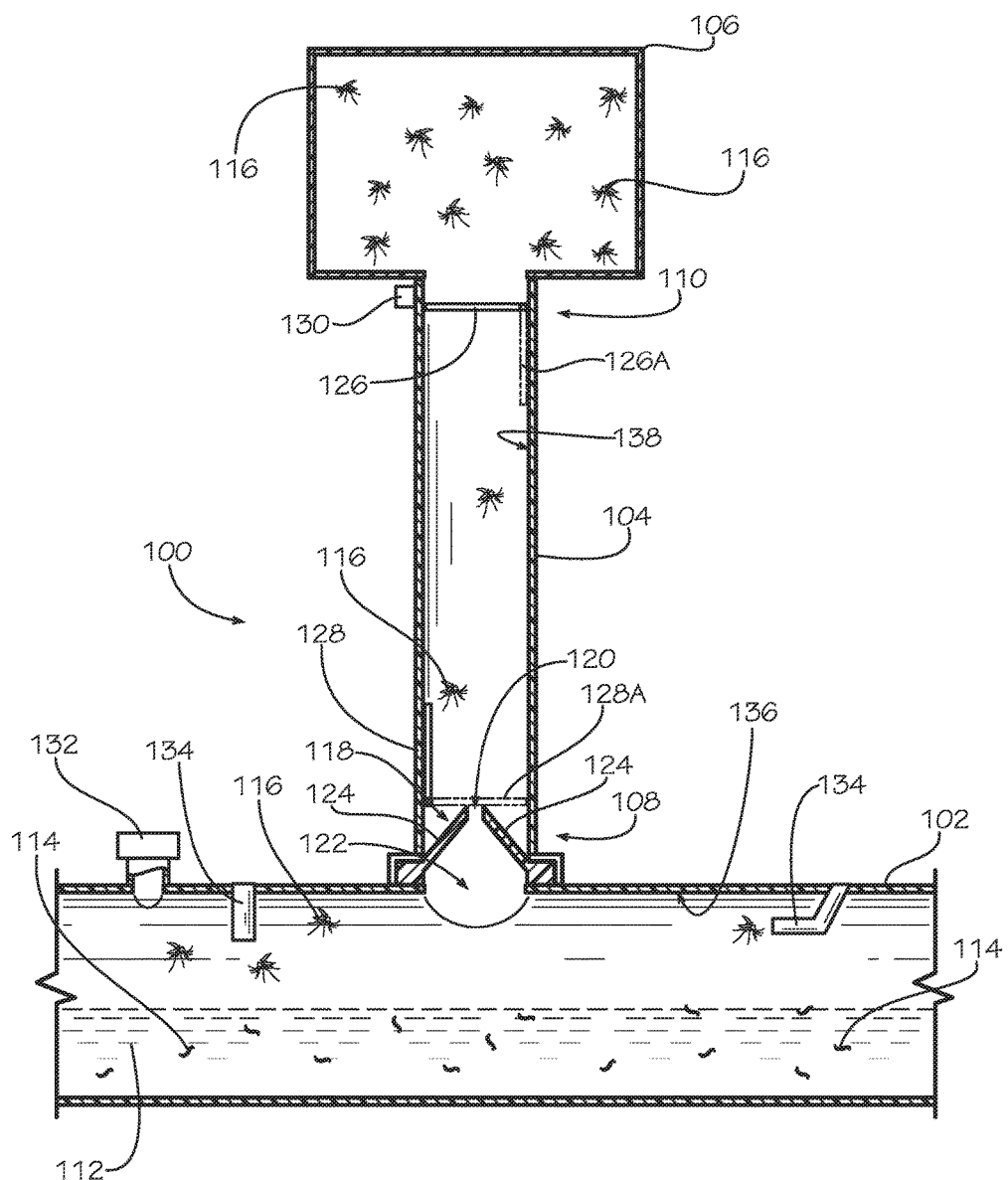
FIG. 2 is a cross-sectional view of a portion the pupae emergence apparatus of FIG. 1, according to aspects of the present disclosure.

FIG. 2 is a cross-sectional view of a portion of the emergence apparatus 100 of FIG. 1, according to an aspect of the present disclosure. As shown in FIG. 2, the tube 104 of the emergence device may be coupled to the pipe 102 at a proximate end 108 of the tube 104. The release container 106 may be coupled of the tube 104 at a distal end 110 of the tube 104. Water 112 and pupae 114 may be positioned within the pipe 102. Adult mosquitos 116 may emerge from the pupae 114 and travel from the pipe 102 into the tube 104. The adult mosquitos 116 may also travel through the length of the tube 104 and into the release container 106.

As shown in FIG. 2, the proximate end 108 of the tube 104 may include a restriction device 118. The restriction device 118 may be designed to permit adult mosquitos 116 to enter the tube 104 from the pipe 102. The restriction device 118 may also restrict the ability for the adult mosquitos 116 to exit the tube 104 and re-enter the pipe 102. The restriction device 118 may be a device that is generally triangular in shape, more particularly the restriction device 118 may be shaped generally like a funnel. The restriction device 118 may include a smaller opening 120 on one end and a larger opening 122 on the other end of the restriction device 118.

The larger opening 122 of the restriction device 118 may be positioned proximate to the pipe 102 and the smaller opening 120 may be positioned further within the tube 104. The larger opening 122 may permit adult mosquitos 116 to exit the pipe 102 and enter the tube 104 by urging the adult mosquitos 116 along the sloped sides 124 of the restriction device 118 and through the smaller opening 120. Adult mosquitos 116 that have passed through the restriction device 118 may be restricted from exiting the tube 104 and re-entering the pipe 102 by the size of the smaller opening 120. In some examples, the restriction device 118 may be a device that blows air within the tube 104 or pipe 102, the direction of air flow may prevent insects from passing from the pipe 102 back into the tube 104.

The adult mosquitos 116 may travel through the tube 104 and into the release container 106 attached to a distal end 110 of the tube 104. A shutter 126 or valve may be positioned at the distal end 110 of the tube 104. The shutter 126 can have an open position which permits access between the distal end 110 of the tube 104 and the release container 106. The shutter 126 can also have a closed position which restricts or prevents access between the tube 104 and the release container 106. The shutter 126 may be mechanical, electric, or any other suitable means for moving from the open position to the closed position. In some aspects, the shutter 126 may be positioned elsewhere within the tube 104. For example, the shutter 126 may be positioned within the release container 106 or the pipe 102.

In FIG. 2 the shutter 126 is shown extending across the diameter of the tube 104 in the closed position. In the closed position, the shutter 126 may prevent the adult mosquitos 116 from exiting the distal end 110 of the tube 104 and entering the release container 106. Dotted lines 126A show the shutter 126 in the open position, according to an aspect of the present invention. Adult mosquitos 116 may exit the distal end 110 of the tube 104 and enter the release container 106 when the shutter 126 is in the open position.

In some aspects, a lower shutter 128 may be positioned at the proximate end 108 of the tube 104. In FIG. 2 the lower shutter 128 is shown in the open position. Adult mosquitos 116 that have emerged from pupae 114 in the pipe 102 may exit the pipe 102, pass through the restriction device 118, and enter the tube 104 when the lower shutter 128 is in the open position. A closed position of the lower shutter 128 is shown by dotted lines 128A, according to an aspect of the invention. As shown in FIG. 2, in some aspects, the lower shutter 128 may be flush with or cover the smaller opening 120 of the restriction device 118 in the closed position. For example, a shutter may be or comprise a butterfly valve or a trap door. In some aspects, the lower shutter 128 may be positioned elsewhere in the tube 104 or coupled to the restriction device 118. For example, in some aspects the lower shutter 128 may be coupled to the restriction device 118 and may extend across the diameter of either the smaller opening 120 or the larger opening 122. In some aspects, the emergence apparatus 100 may include one or both of the shutter 126 and lower shutter 128. In some aspects, additional shutters may be included.

The emergence apparatus 100 may also include a sensor 130 positioned at the distal end 110 of the tube 104, as shown in FIG. 2. In some aspects, the sensor 130 may be positioned elsewhere proximate to the release container 106. The sensor 130 can detect an adult mosquito 116 passing by the sensor which may indicate the adult mosquito is entering the release container 106. The sensor 130 may include a sensing device, a processor, memory, and a wireless communication device. In some aspects, the sensor 130 may include analog or digital electronics. The sensor 130 may be communicative coupled to the shutter 126 via a wired or wireless communication link. The sensor 130 may send a signal to the shutter 126 that causes the shutter 126 to move to an open position or a closed position. In some aspects, the sensor 130 may send a voltage signal, current signal, or other pulse signal to the shutter 126. The shutter 126 may close in response to the signal. For example, the sensor 130 may send a voltage signal that activates a motor of the shutter 126 and causes the shutter 126 to move to the closed position.

As shown in FIG. 2, the sensor may be positioned outside of the tube 104, for example in an aspect in which the tube 104 is transparent providing the sensor 130 with a view of the interior region of the tube 104. In some aspects, the sensor 130 may be positioned outside of the release container 106. In some aspects, the sensor 130 may be positioned inside either the tube 104 or the release container 106. In still yet other aspects, the sensor 130 may be positioned on the outside of the tube 104 or release container 106 and may have a view of the interior of the tube 104 or release container 106 via a viewing window.

The sensor 130 may also count or determine the total number of adult mosquitos 116 that it has detected as entering the release container 106. In some aspects, the sensor 130 may also detect an adult mosquito 116 exiting the release container 106 and re-entering the tube 104. The sensor 130 may update the total number of adult mosquitos 116 counted as entering the release container 106 to reflect the adult mosquito 116 has left the release container 106. In some aspects, the sensor 130 may store the total number of adult mosquitos 116 that it has detected as entering the release container 106 in memory. The sensor 130 may compare the total number of adult mosquitos 116 that it has detected as entering the release container 106 to a pre-set value. The sensor 130 may receive the pre-set value during an initial set-up of the emergence apparatus 100 or at a later time. The pre-set value may correspond to a number of adult mosquitoes 116 that are desired to be captured in the release container 106. For example, in some aspects, it may be desirable to have a consistent number of adult mosquitos 116 captured within the release containers 106 for release later into the environment.

The sensor 130 may transmit instructions to the shutter 126 to move from the open position to the closed position. In some aspects, the sensor 130 may transmit instructions to the shutter 126 to move to the closed position in response to the sensor 130 determining that the total number of adult mosquitoes 116 that it has counted as entering the release container 106 is equal to the pre-set value. In some aspects, the sensor 130 may transmit instructions to the shutter 126 to move to the closed position in response to determining the total number of adult mosquitos 116 detected as entering the release container 106 is greater than or equal to the pre-set value.

In some aspects, the sensor 130 may transmit instructions to the shutter 126 to move to the closed position in response to other characteristics monitored by the sensor 130. For example, if the total number of adult mosquitos 116 that have entered the release container 106 has not increased for a pre-determined period of time, the sensor 130 may instruct the shutter 126 to move to the closed position. In some aspects, the sensor 130 may also gather data that may be used to determine if the adult mosquito is a male mosquito or a female mosquito. In some aspects, the sensor 130 may instruct the shutter 126 to open or close in response to the determination of the sex of the adult mosquito 116. In some aspects, the sensor 130 may be in communication with a computing device located away from the emergence apparatus 100. The computing device may count or determine the total number of adult mosquitos 116 detected by the sensor 130 as entering the release container 106. The computing device may be in wired or wireless communication with the shutter 126 and may provide instructions to the shutter 126 to open or close in response to the total number of adult mosquitos 116 counted in the release container 106.

The pipe 102 of the emergence apparatus 100 may include features that may increase the health or viability of the adult mosquitos 116. In some aspects, the pipe 102 may include an access valve 132. The access valve 132 may be an opening that is covered by a removable cap, or other suitable means for providing access to the interior region of the pipe 102. Though only one access valve 132 is shown in FIG. 2, more or fewer access valves 132 may be used. The access valve 132 may be used to add sugar or other nutritional supplements into the water 112 to aid in the emergence of the pupae 114 into adult mosquitos 116. In some aspects, the access valve 132 may be used to inject water into the pipe 102 to raise the water level and encourage any adult mosquitos 116 within the pipe 102 to fly into the tubes 104. Similarly, in some aspects, air may be blown into the pipe 102 through the access valve 132 to push the adult mosquitos 116 out of the pipe 102 and into the tubes 104. In some aspects, the access valve 132 may be used to remove water from the pipe 102 to lower the water level and/or drain the water 112. For example, in some aspects the water 112 may be drained and replaced via the access valve 132. In some aspects, the water 112 may be a temperature that may aid increase the health or viability of the adult mosquitos, including but not limited to about 25 and about 30 degrees Celsius. For example, the water 112 may be about 28 degrees Celsius in some aspects.

In some aspects, the pipe 102 may include other features that may enhance the fitness of the adult mosquitos 116 by producing healthy adult mosquitos 116. For example, in some aspects the pipe 102 main include ideal water conditions, temperature, and/or lighting for pupae 114 to emerge into adult mosquitos 116. The lighting may include on and off cycles that may aid in the synchronizing of the adult mosquitos 116. In some aspects, the lighting may urge adult mosquitos 116 in a desired direction within the emergence apparatus 100. In some aspects, the pipe 102 may include resting surfaces (or roosting surfaces) that an adult mosquito 116 may rest on, for example resting surfaces 134 shown in FIG. 2.

In some aspects more or fewer resting surfaces 134 may be used and the resting surfaces 134 may be positioned in different locations within the pipe 102 and/or the tube 104. In some aspects, all or part of the inner surface of the pipe 102 may include a treatment 136. In some aspects, the treatment 136 may reduce contamination, for example be antibacterial. In some aspects, the treatment 136 may prevent or in the alternative aid in mosquito resting and roosting. In some aspects, the treatment 136 may be provided on all or part of the inner surface of the tube 104. In other aspects, a different treatment 138 may be provided on the inner surface of the tube 104.

Figure 3:
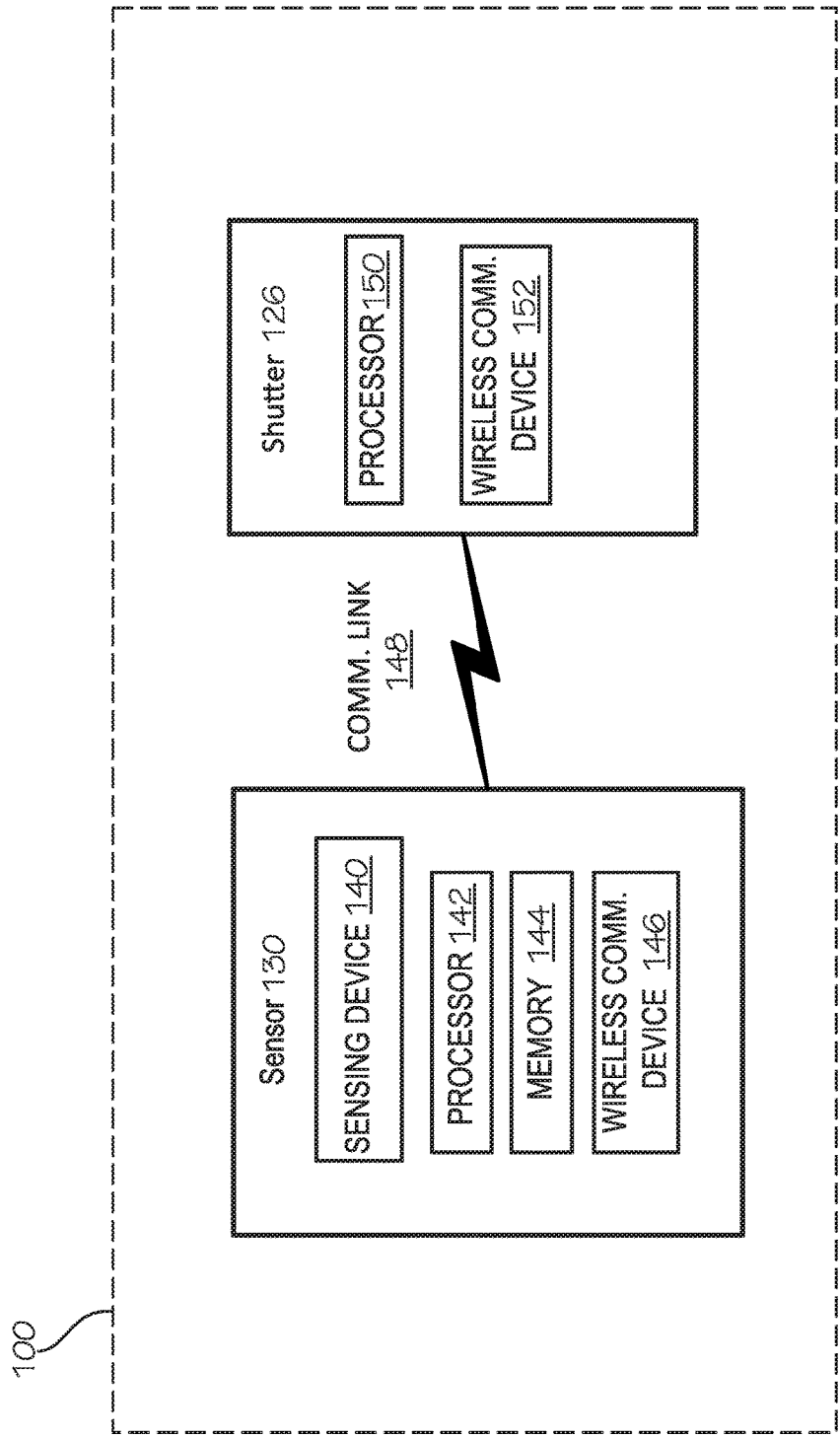
FIG. 3 is a block diagram of the pupae emergence apparatus of FIG. 1, according to aspects of the present disclosure.

FIG. 3 is a block diagram of the emergence apparatus 100 according to aspects of the present disclosure. The emergence apparatus 100 includes the shutter 126 and the sensor 130. The sensor 130 may detect an adult mosquito passing by the sensor 130 as it enters the release container 106. The sensor 130 may include a sensing device 140, a processor 142, memory 144, and a wireless communication device 146. The sensor 130 may be communicatively coupled to the shutter 126 by a communication link 148. The communication link 148 may be a wireless communication link and may include wireless interfaces such as IEEE 802.11, Bluetooth, or radio interfaces for accessing cellular telephone networks (e.g., transceiver/antenna for accessing a CDMA, GSM, UMTS, or other mobile communications network). In other aspects, the communication link 148 can be wired and can include interfaces such as Ethernet, USB, IEEE 1394, fiber optic interface, voltage signal line, or current signal line.

As described above with reference to FIG. 2, elements of the sensor 130, including the sensing device 140, may detect that an adult mosquito 116 has passed by the sensor 130 and entered the release container 106. In some aspects, the sensing device 140 of the sensor 130 may be an optical sensing device (e.g., photosensor, camera, laser, or radar), an acoustic sensing device (e.g. a microphone or ultrasound sensor), or any other suitable sensing device for detecting an adult mosquito 116. The sensor 130 may determine the total number of adult mosquitos 116 that it has detected. In some aspects, the sensing device 140 may determine the number of adult mosquitos 116 of a certain sex that it has detected as entering the release container 106. In other aspects the processor 142 may collect the data gathered by the sensing device 140 and the processor 142 may determine the total number of adult mosquitos 116 that have been detected as entering the release container 106. In some aspects the sensing device 140 or the processor 142 may determine the sex of the adult mosquitos that have entered the release container 106. In still yet other aspects, a computing device that includes a processor may be coupled to the sensor 130. The computing device may determine the total number of adult mosquitos 116 that have been detected as entering the release container 106. In some aspects computing device may determine the sex of the adult mosquitos that have entered the release container 106.

The sensor 130 may transmit a signal to the shutter 126 via the communication link 148, the signal may cause the shutter 126 to move from the open position to the closed position. For example, the sensor 130 may transmit a signal to the shutter 126 in response to determining the number of adult mosquitoes that it has counted as entering the release container is equal to a pre-set value or in response to determining the number of adult mosquitos of a certain sex have been counted as entering the release container is equal to a pre-set value. In some aspects, the sensor 130 may transmit a signal to the shutter 126 to move to the closed position in response to determining the detected number of adult mosquitos (or number of adult mosquitos of a certain sex) in the release container is greater than or equal to the pre-set value. In some aspects, a computing device may transmit a signal to the shutter 126 to move to the closed position. For example, in response to a user's input at the computing device. In aspects in which the communication link 148 is a wireless communication link, the wireless communication device 146 may transmit the signal to the communication link 148.

In some aspects, the shutter 126 may receive the signal from the sensor 130 and may move to an open or a closed position in response to the signal. For example, the signal may be a voltage signal that causes a motor of the shutter 126 to actuate and move the shutter 126 to a closed position. In some aspects, the shutter 126 may include a processor 150 and a wireless communication device 152. The shutter 126 may receive a signal from the sensor 130 via the communication link 148. In aspects in which the communication link 148 is wireless, the wireless communication device 152 of the shutter 126 may receive a digital signal and transmit the digital signal to the processor 150 for processing. The processor 150 may convert the digital signal into an electrical signal that may control the motor of the shutter and thereby control the position of the shutter 126. In some aspects, the shutter 126 may be moved from the open position to the closed position manually.

Figure 4:
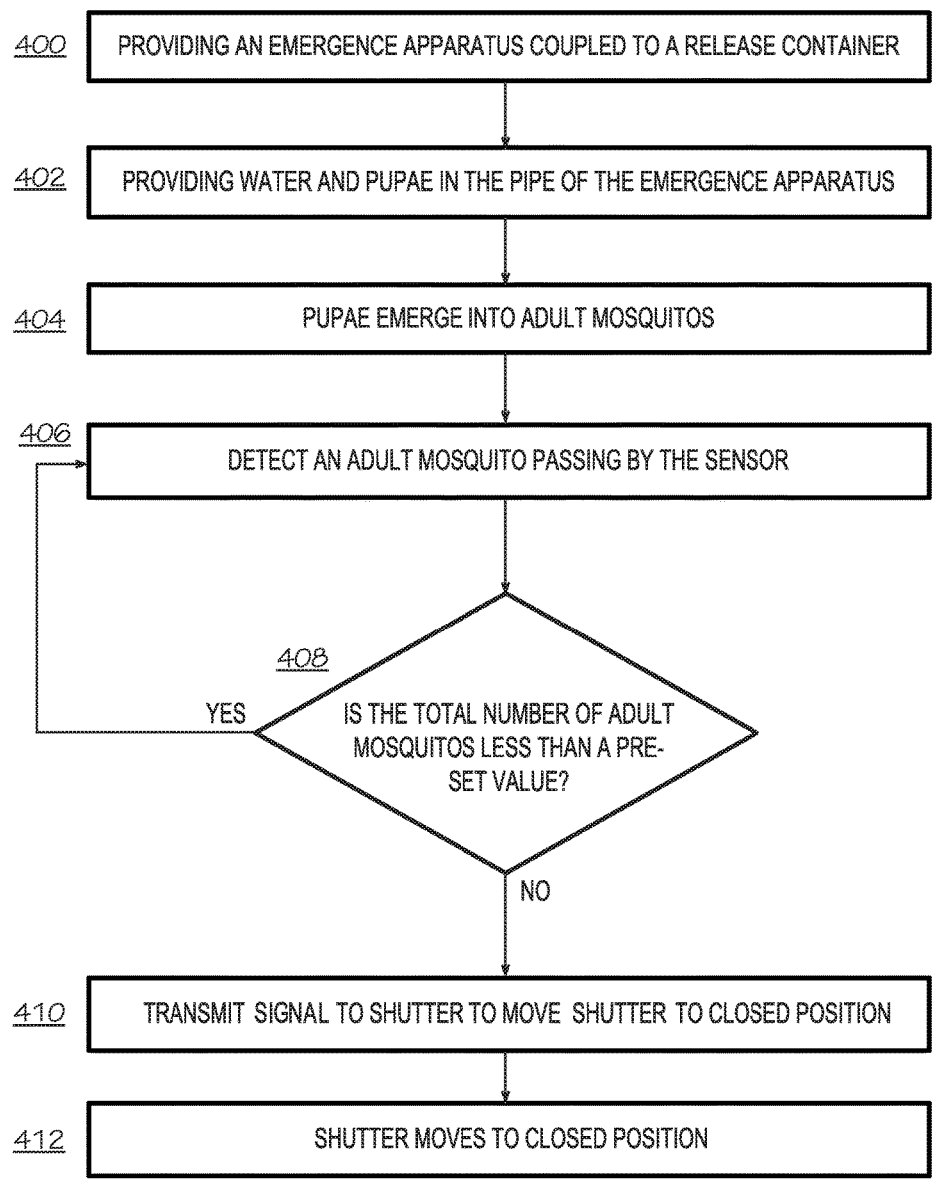
FIG. 4 is a flow chart of a process for raising pupae into adult mosquitos and collecting a desired number of adult mosquitos in a release container using the pupae emergence apparatus of FIG. 1, according to aspects of the present disclosure.

FIG. 4 is a flow chart of a process for raising pupae into adult mosquitos and gathering a desired number of adult mosquitos in a release container. The process is described with reference to the figures described herein, though other implementations are possible without departing from the scope of the present disclosure. In block 400, the emergence apparatus 100 coupled to the release containers 106 is provided. The emergence apparatus 100 may include a pipe 102 and one or more tubes 104, the tubes 104 may be coupled to one or more release containers 106.

At block 402 water and pupae are provided in the pipe 102. As described above with reference to FIG. 2, the pipe 102 may also include features that increase the emergence of pupae 114 into adult mosquitos 116, including for example temperature, lighting, and nutritional additives that can increase the fitness of the adult mosquitos 116.

At block 404, the pupae 114 may emerge into adult mosquitos 116 and may exit the pipe 102 and enter the tube 104. The adult mosquitos 116 may fly towards the release containers 106. In some aspects, the release containers 106 may include features that may attract the adult mosquitos 116 to the release containers 106, for example but not limited to scents, lighting, and/or sounds that attract adult mosquitos 116.

At block 406, the sensor 130 may detect an adult mosquito 116 passing by the sensor 130 which may indicate the adult mosquito 116 entered the respective release container 106. The sensor 130 may detect the adult mosquito 116 by any suitable means, including by acoustic, optical, or other methods as described further above with respect to FIGS. 2 and 3. After detecting each adult mosquito 116, the sensor 130 may increment a counter that tracks the number of detected adult mosquitoes. In some aspects, the sensor 130 may store the total number of adult mosquitos 116 it detected as entering the release container 106. In some aspects, the sensor 130 may transmit the total number of detected adult mosquitos 116 in the release container 106 to a computing device located away from the emergence apparatus 100. After incrementing the counter to track the total number of adult mosquitos it detects as entering the release container 106, the sensor 130 may proceed to block 408.

At block 408, the sensor 130 may determine if the total number of adult mosquitos 116 it detected as entering the release container 106 is less than a pre-set value. If at block 408 the sensor 130 determines that the current number of adult mosquitos 116 it detected as entering the release container 106 is less than the pre-set value, the sensor 130 may do nothing and the process may return to block 406 when the sensor 130 detects another adult mosquito passing by the sensor 130. In some aspects, the sensor 130 may transmit instructions to the shutter 126 after determining at block 408 that the total number of adult mosquitos 116 it detected as entering the release container 106 is less than a pre-set value.

If at block 408, the sensor 130 determines that the total number of adult mosquitos 116 it detected as entering the release container 106 is greater than or equal to the pre-set value, the process may move to block 410. At block 410, the sensor 130 may transmit a signal to the shutter 126 to close the shutter 126. The sensor 130 may transmit the signal to the shutter 126 via the communication link 148.

At block 412, the shutter 126 may close in response to the signal from the sensor 130. With the shutter 126 in the closed position the adult mosquitos 116 within the release container 106 may be prevented from exiting the release container 106. The release container 106 may contain a desired number of adult mosquitos 116. The desired number may correspond to the pre-set value. The release container 106 may be removable from the tube 104 such that the release container 106 may be moved to another location, for example a location where the adult mosquitos 116 are to be released. After removal of the release container 106, the adult mosquitos 116 within the tube 104 may be prevented from exiting the distal end 110 of the tube 104 by the shutter 126.

In some aspects, after block 412, when shutter 126 is in the closed position, a new release container 106 may be coupled to the end of the tube 104. The sensor 130 may transmit instructions to the shutter 126 to position the shutter in the open position following the coupling of the new release container 106. Adult mosquitos 116 may enter the new release container 106 when the shutter 126 is in the open position. In some aspects, the sensor 130 may transmits the instructions to the shutter 126 to move to the open position in response to receiving a signal from another source, for example but not limited to a signal produced in response to a button of the shutter 126 being pressed or a signal from a computing device positioned away from the emergence apparatus 100. In still yet other aspects, the shutter 126 may transmit the instruction to the shutter 126 in response to determining that a new release container 106 has been coupled to the tube 104.

Figure 5:
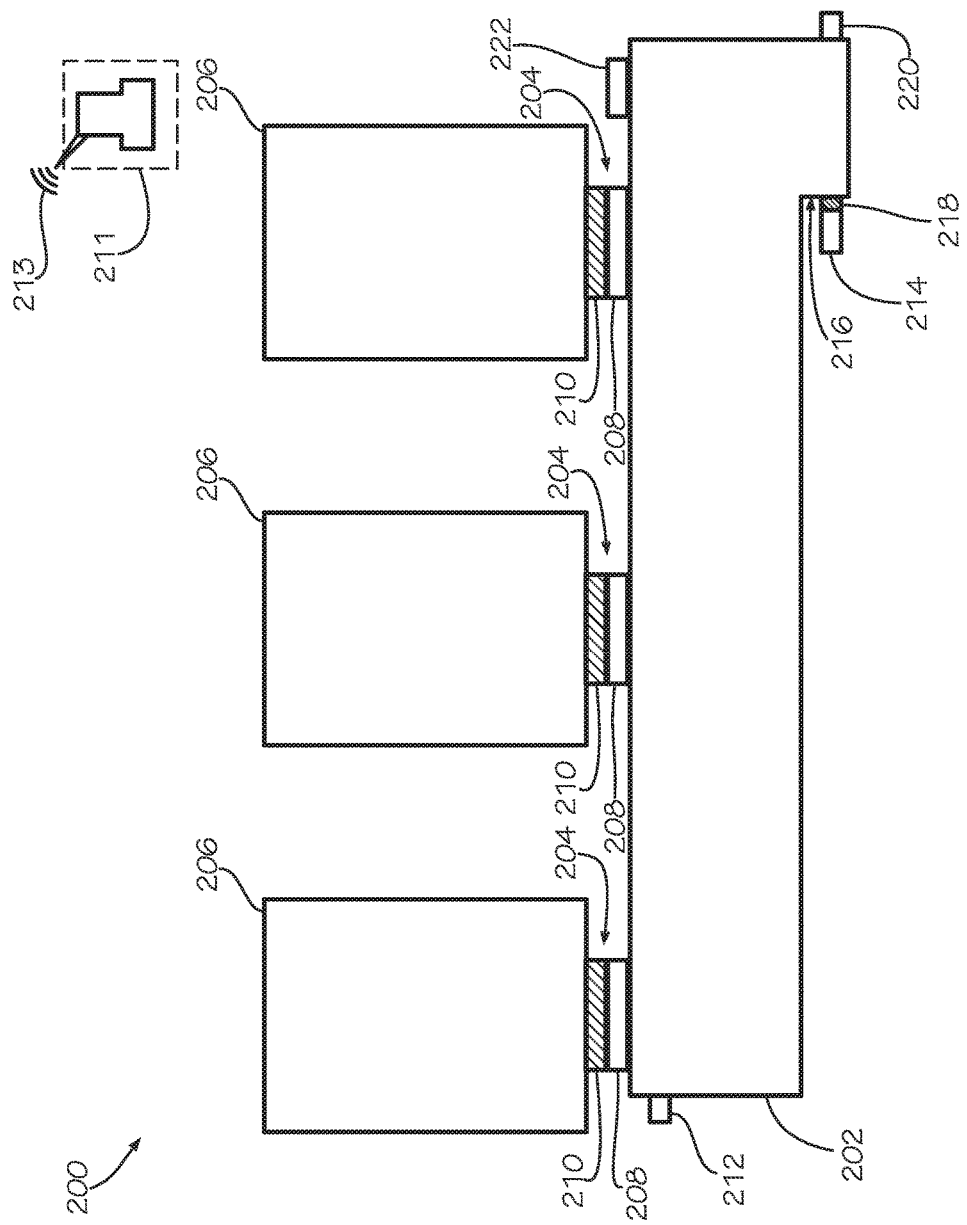
FIG. 5 is a cross-sectional diagram of a pupae emergence apparatus, according to aspects of the present disclosure.

FIG. 5 is a perspective view of an emergence apparatus 200 for storing pupae as they develop into adult mosquitos according to an aspect of the present disclosure. In some aspects, the pupae of other insects may be raised in the emergency device. The emergence apparatus 200 may include a vessel 202, such as pipe in which pupae and water may be placed. The emergence apparatus 200 may also include one or more passageways 204 that connect the vessel 202 to one or more release containers 206. The passageways 204 may be of any suitable length, for example in some aspects the passageways 204 are each approximate 0.5 inch in length, though other suitable lengths may be used, including for example a length between 0.5 inch and 2 inches, between 2 inches and 6 inches, between 6 inches and 12 inches, or any other suitable length. In some aspects, the release containers 206 may be coupled directly to the vessel 202, and the passageways 204 may be the opening between the release containers 206 and the vessel 202. For example, in an aspect of the emergence apparatus 200 that includes multiple sensors or additional features, the passageways 204 may be between longer (e.g., between about 4 inches and about 7 inches) to accommodate the multiple sensors and additional features. A release container 206 may be coupled to each of the passageways 204 of the emergence apparatus 200. The passageways 204 may connect an interior region or space of the vessel 202 and an interior region or space of the release containers 206. The pupae within the vessel 202 may emerge into adult mosquitos within the vessel 202. The adult mosquitos may fly from the vessel 202 through the passageways 204 and into the release containers 106.

A valve or shutter 208 may be positioned proximate to the opening between each of the passageways 204 and the vessel 202. In some aspects the shutter 208 may be positioned within the passageway 204, including either proximate to the vessel 202 or proximate to the release container 206. The shutter 208 may control access from the vessel 202 to each of the passageways 204 individually, and thereby to each of the release containers 206.

The emergence apparatus 200 may also include a sensor 210 positioned within each of the passageways 204. In some aspects, the sensor 210 may be positioned elsewhere, including for example, but not limited to, within the release container 206 or within the vessel 202. The sensor 210 may extend around all or part of the circumference of each respective passageway 204. In some aspects, additional sensors may be used, for example a camera, an acoustic sensor, an optical sensor, or other sensors for gathering additional data related to the surroundings and/or the adult mosquito.

In some aspects, each respective sensor 210 may be positioned above each respective shutter 208 and proximate to the opening between the respective passageway 204 and the respective release container 206. Each sensor 210 may detect an adult mosquito passing by the sensor 210 and entering the adjacent release container 206. The sensor 210 may transmit a signal to the shutter 208 to move from an open position to a closed position in response to the sensor 210 determining a desired number of adult mosquitos have entered the adjacent release container 206. In some aspects, the sensor 210 may transmit a signal to computing device 211 located away from the apparatus. The signal may indicate the sensor 210 detecting an adult mosquito or may indicate the number of adult mosquitos the sensor 210 has detected as entering the adjacent release container 206. The computing device 211 may be communicatively coupled to the sensor 210 via a wireless communication link 213. The wireless communication link 213 may include wireless interfaces such as IEEE 802.11, Bluetooth, or radio interfaces for accessing cellular telephone networks (e.g., transceiver/antenna for accessing a CDMA, GSM, UMTS, or other mobile communications network). In other aspects, a wired communication link may be used instead of the wireless communication link 213, the wired communication link may include interfaces such as Ethernet, USB, IEEE 1394, fiber optic interface, voltage signal line, or current signal line.

The computing device 211 may also be communicatively coupled to the shutter 208. The computing device 211 may be communicatively coupled to the shutter 208 via the wireless communication link 213, or via another communication link. The computing device 211 may transmit an instruction signal to the shutter 208. The instruction signal may control the position of the shutter 208. Thus, in some examples, a computing device 211 controls the position of the shutter 208 by sending a signal to the shutter 208 to open or to close. For example, the computing device 211 may receive user input that determines the instruction signal that is sent to the shutter 208. The computing device 211 may include a display that may display data related to the signal received from the sensor 210, for example but not limited to the number of adult mosquitos that have been detected by each of the sensors 210. In still yet other aspects, the position of the shutter 208 may be moved between the open and the closed position manually.

The vessel 202 may contain features that increase the emergence of pupae into adult mosquitos and improve the ability to maintain the emergence apparatus 200. In some aspects, the vessel 202 may include one or more access valves, for example input water valve 212. The input water valve 212 may provide access to the interior region of the vessel 202 and may permit adding water to the interior region of the vessel 202. Water may be added to the interior of the vessel 202 to replace water that was drained from the vessel 202. Water may also be added to the interior of the vessel 202 to increase the height of the water and encourage mosquitos to exit the vessel 202 and enter the passageways 204 and release containers 206.

The vessel 202 may also include other access valves, for example a partial drainage valve 214. The partial drainage valve 214 may be positioned in a bottom region of the vessel 202. As shown in FIG. 5, the partial drainage valve 214 may be positioned in a lower extension 216 of the vessel 202. The lower extension 216 of the vessel 202 may be a portion of the vessel 202 that extends below the rest of the vessel 202. The partial drainage valve 214 may also contain a filter or mesh 218 element that may prevent pupae from passing through the partial drainage valve 214. The filter 218 may be sized such that the openings in the filter 218 are smaller than the size of the pupae. The filter 218 may thus permit water to drain from the vessel 202 through the partial drainage valve 214 while preventing pupae from being drained with the water out of the vessel 202. Water may be reintroduced into the vessel 202 via the input water valve 212.

The vessel 202 may include an access valve that is a full drainage valve 220. The full drainage valve 220 may be positioned in a bottom region of the vessel 202. As shown in FIG. 5, the full drainage valve 220 may be positioned in the lower extension 216 of the vessel 202. The full drainage valve 220 may permit water, pupae, solid waste, and other material from the interior region of the vessel 202 to drain out of the vessel 202 through the full drainage valve 220. The full drainage valve 220 can be used to fully empty the interior region of the vessel 202. Water may be reintroduced into the vessel 202 via the input water valve 212. Thus, the vessel 202 can be emptied, cleaned, and refilled for repeated use.

In some aspects, the vessel 202 may also include a water level sensor 222. The water level sensor 222 can detect the water level within the interior of the vessel 202. In some aspects, the water level sensor 222 may be an ultrasonic transducer, a laser level transmitter, a radar level transmitter, or any other suitable sensor for determining water level within the interior of the vessel 202. The water level sensor 222 may be communicatively linked to a computing device, for example the computing device 211. The computing device may include a display that displays information related to the data collected by the water level sensor 222, including for example the height of the water in the vessel 202. The water level sensor 222 may include or may be coupled to an alarm or other indication device that indicates when the water level within the interior of the vessel is outside of a preset range. The water level sensor 222 may aid in controlling the draining of water from the interior region of the vessel 202. The water level sensor 222 may also aid in the refilling of the interior region of the vessel 202 to a desired water level. In some aspects, the water level sensor may aid in the flooding of the interior of the vessel 202 (e.g., the raising of the water level) to encourage the adult mosquitos to enter the passageways 204 and the release containers 206.

As discussed above, one or more suitable devices according to this disclosure may include a processor or processors. The processor may be in communication with a computer-readable medium, such as a random access memory (RAM) coupled to the processor. The processor executes computer-executable program instructions stored in memory. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor with computer-readable instructions. Other examples of media comprise, but are not limited to memory chips, ROM, RAM, ASICs, configured processors, or any other medium from which a computer processor can read. The processor, and the processing, described may be in one or more structures, and may be dispersed through one or more structures. The processor may comprise code for carrying out one or more of the methods (or parts of methods) described herein.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one aspects," "in some aspects," "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

What is claimed is:

1. An emergence apparatus, comprising:
   a vessel having an interior space to receive water and insect pupae;
   a first release container connected to the vessel;
   a first sensor positioned proximate to the first release container to detect an adult insect passing by the first sensor and into the first release container; and
   a first shutter positioned proximate to an entrance to the first release container, the first shutter having an open position and a closed position to control access between the vessel and the first release container.

2. The emergence apparatus of claim 1, further comprising:
   a second release container connected to the vessel;
   a second sensor positioned proximate to the second release container to detect an adult insect passing by the second sensor and into the second release container; and
   a second shutter positioned proximate to an entrance to the second release container, the second shutter having an open position and a closed position to control access between the vessel and the second release container.

3. The emergence apparatus of claim 2, further comprising:
   a computing device configured to receive a first input signal from the first sensor and a second input signal from the second sensor,
   wherein the first shutter is configured to receive a first output signal from the computing device to position the first shutter in one of the open position or the closed position, and
   wherein the second shutter is configured to receive a second output signal from the computing device to position the second shutter in one of the open position or the closed position.

4. The emergence apparatus of claim 3, wherein the computing device is configured to determine a total number of adult insects detected by each respective sensor based on the first input signal and the second input signal.

5. The emergence apparatus of claim 3, wherein the computing device is configured to compare the total number of adult insects detected by each of the first sensor and the second sensor to a pre-set value.

6. The emergence apparatus of claim 5, wherein the first output signal instructs the first shutter to move to the closed position in response to determining the total number of adult insects detected by the first sensor is greater than or equal to the pre-set value.

7. The emergence apparatus of claim 5, wherein the second output signal instructs the second shutter to move to the closed position in response to determining the total number of adult insects detected by the second sensor is greater than or equal to the pre-set value.

8. The emergence apparatus of claim 1, further comprising:
   a computing device configured to receive a first input signal from the first sensor and,
   wherein the first shutter is configured to receive a first output signal from the computing device to position the first shutter in one of the open position or the closed position.

9. The emergence apparatus of claim 8, wherein, the first input signal received by the computing device from the first sensor indicates an adult insect was detected by each respective sensor.

10. The emergence apparatus of claim 1, wherein the first release container further comprises an attractant for attracting an insect to enter the first release container.

11. The emergence apparatus of claim 1, further comprising a first passageway connecting the vessel to the first release container.

12. The emergence apparatus of claim 11, further comprising a restriction device comprising a first opening on one end proximate to the vessel and a second opening on the other end of the restriction device proximate to the first passageway, wherein the first opening is larger than the second opening for permitting an insect to enter the first passageway from the vessel while restricting the insect from entering the vessel from the first passageway.

13. The emergence apparatus of claim 11, wherein the first shutter is positioned within the first passageway.

14. An emergence apparatus, comprising:
   a vessel having an interior space to receive water and insect pupae;
   a passageway, the passageway connecting the vessel to a release container;
   a sensor positioned proximate to the release container to detect an adult insect passing by the sensor and into the release container;
   a shutter positioned in the passageway, the shutter having an open position and a closed position to control access between the vessel and the release container; and
   a computing device configured to receive an input signal from the sensor.

15. The emergence apparatus of claim 14, further comprising a water level sensor for detecting a height level of the water within the interior space of the vessel.

16. The emergence apparatus of claim 14, further comprising an access valve that provides access to the interior space of the vessel for adding water to the interior space of the vessel.

17. The emergence apparatus of claim 14, further comprising an access valve that is positioned at a lower region of the vessel for draining matter from the interior space of the vessel.

18. The emergence apparatus of claim 14, wherein the sensor includes the computing device.

19. The emergence apparatus of claim 14, wherein the computing device is configured to determine a total number of adult insects detected by the sensor as passing by the sensor.

20. The emergence apparatus of claim 19, wherein the computing device is configured to compare the total number of adult insects detected by the sensor to a pre-set value, and wherein the computing device is configured to transmit the output signal to the shutter to position the shutter in the closed position in response to determining the total number of detected adult insects is at least equal to the pre-set value.

* * * * *